United States Patent
Lassalle et al.

(10) Patent No.: US 7,344,868 B2
(45) Date of Patent: Mar. 18, 2008

(54) METHOD FOR SYNTHESIZING CERAMIDE-TYPE COMPOUNDS

(76) Inventors: Laurent Lassalle, 13 rue Anatole France, F27780 Garennes sur Eure (FR); Florent Yvergnaux, 3 rue Chevenotte, F28100 Dreux (FR)

( * ) Notice: Subject to any disclaimer, the term of this patent is extended or adjusted under 35 U.S.C. 154(b) by 32 days.

(21) Appl. No.: 10/559,713

(22) PCT Filed: Jun. 3, 2004

(86) PCT No.: PCT/FR2004/001375

§ 371 (c)(1),
(2), (4) Date: Dec. 5, 2005

(87) PCT Pub. No.: WO2004/108659

PCT Pub. Date: Dec. 16, 2004

(65) Prior Publication Data

US 2006/0121583 A1     Jun. 8, 2006

(30) Foreign Application Priority Data

Jun. 3, 2003   (FR) ................................. 03 106661

(51) Int. Cl.
 C12P 13/02   (2006.01)
 C12P 7/62    (2006.01)
(52) U.S. Cl. ....................................... 435/129; 435/135
(58) Field of Classification Search ............... 564/192, 564/204, 215; 560/206, 250; 435/129, 134, 435/135
See application file for complete search history.

(56) References Cited

FOREIGN PATENT DOCUMENTS

CA      2276902      *    1/2000

OTHER PUBLICATIONS

Maugard et al., Enzymatic synthesis of glycamide surfactants by amidification reaction, Tetrahedron, vol. 53, Issue 14, Apr. 7, 1997, pp. 5185-5194.*
Bartling et al., Lipase-catalyzed synthesis of geranyl acetate in n-hexane with membrane-mediated water removal, Biotechnology and Bioengineering vol. 75, Issue 6, Date: Dec. 20, 2001, pp. 676-681.*

* cited by examiner

*Primary Examiner*—Karl Puttlitz
(74) *Attorney, Agent, or Firm*—Charles A. Muserlian

(57) ABSTRACT

The invention relates to the fields of fatty substance chemistry, specifically of the ceramide-type compound synthesis. The invention resides substantially in the synthesis of ceramide-type compounds. Specifically, the aim of the invention is a new enzymatic synthesis method, comprising at least one amidification step and one esterification step, achieved through lipases, among fatty acids and/or esters thereof and amino alcohols. The resulting ceramide-type compounds can be used as cosmetic and/or pharmaceutical compositions, in particular as dermatological compositions in conjunction or in admixture with one or more suitable cosmetic and/or pharmaceutical excipients or carriers. The method has an interest particularly in the synthesis of active compounds useful in the fields of cosmetology and/or pharmacology and specifically of dermatology.

12 Claims, No Drawings

METHOD FOR SYNTHESIZING CERAMIDE-TYPE COMPOUNDS

This application is a 371 of PCT /FR2004/001375 filed Jun. 3, 2004.

This invention relates to the field of chemistry of fats and more particularly to processes of enzymatic synthesis of ceramide-type compounds.

This invention substantially lies in the synthesis of ceramide-type compounds having the general formula (I).

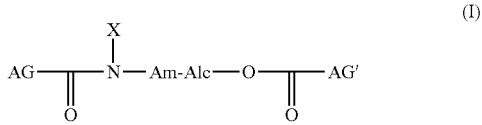

wherein the group Am-Alc figures a C2 to C6 carbon chain, preferably saturated, linear or optionally branched, stemming from an amino-alcohol; X figures a hydrogen atom or a C1 to C4 carbon chain, optionally hydroxylated on the 2' and/or following positions of the amino group; and in which each of the groups AG and AG' figures a C4 to C30 carbon chain, saturated or unsaturated, stemming from a fatty acid or a fatty acid ester; the two groups AG and AG' may be identical or different.

More precisely, this invention has as a subject matter a novel method of enzymatic synthesis of ceramide-type compounds from fatty acids and/or esters of fatty acid and amino-alcohol, including at least a step of amide formation and a step of esterification, both being performed by enzymatic way, in any order.

Ceramides belong to the most important lipidic constituents of *stratum corneum*. They are constituted of a long carbon chain linked to a fatty acid through an amide bond. They are normally present at a state of spurs in the tissues where they have significant biological effects.

Due to the fact that they exert a vital role in the conservation of the permeability of tissues against water, ceramides are closely linked to the phenomenon of cutaneous ageing. In fact it is known that the skin aspect is substantially linked to the water content of its various layers. Now the spoiling of membrane lipids, namely resulting of the use of detergents frequently responsible with their elimination, results in the increase of water loss. Moreover, this destruction of the cutaneous barrier leads to an increase of the cutaneous sensibility and to a potential irritation (see Kersher M. et al., *Eur. J. Dermatol.* 1991, 139-143, Imokawa G et al., *J. Soc. Cosmet. Chem.* 1989, 40; 273-285). Various studies such as those disclosed in U.S. Pat. No. 5,470,671 and WO 95/34531 as well as in the publication of R. D. Petersen *Cosm. Toil.* (1992) 107, 45 have shown that the topical application of ceramides allows the balance resulting of their elimination or their degradation. These compounds then have a great usefulness, namely in the field of cosmetology and dermatology.

Natural constituents of almost all the living beings, ceramides may be obtained by extraction from animals (Lambes H., 2$^{nd}$ *ASCS*, 1995), 106-125, from vegetals (WO 92-21321 to Rousset G. Inocosm Lab.) or from yeasts (WO 94-10131 to Casey et al. (Unilever)). However this methods of extraction are often lengthy and restricted due to the availability of the natural resources. This also increases the cost of the ceramides thus obtained.

Many analogs of natural ceramides, also named pseudo-ceramides, have been consequently been synthesized through chemical way. The pseudo-ceramides or ceramide-type compounds are like ceramides but not identical. So, in European patent IP 028 281 (Ohashi Yukihiro al., Kao Corp., 1988) has been disclosed a method of synthesis of pseudo-ceramides through a reaction between a glycidyl ether and an amino-alcohol which is further substituted by a fatty acid through an amide bond. Three consecutive steps are therefore needed for obtaining such pseudo-ceramides.

In U.S. Pat. No. 5,221,757 (Ohashi Yukihiro, Kao Corm. 1993) has also been disclosed a similar synthesis of pseudo-ceramides through from 2 to 6 steps, by a reaction between a glycidyl ether, an amino-alcohol and a fatty acid. This method of synthesis however appears very costly, relatively complicated and not constituting a satisfactory solution for the synthesis of various structures.

Another patent—WO 92/03129 (Hannun Yusuf et. al., Univ. Duke 1992) shows the synthesis of pseudo-ceramides having a structure close to that of natural ceramides. However this method is too complex to be performed at industrial scale.

In French patent application FR 2757853 to Pacific Corporation (1998) has been set out a method of chemical synthesis of compounds very close to natural ceramides. This document enumerates, without further precisions, the structures of natural ceramides derivatives of sphingosins, and therefore hydroxylated in alpha-position on both chains.

According to completely different method disclosed in European patent EP 0884 305 (L'OREAL, 1998), derivatives of ceramide type may have been synthesized by reacting, under microwaves, a fatty acid with an amino-alcohol of defined structure. However, such a synthesis needs to be carried out at high temperature, which is not always suitable for unstable compounds, such as the unsaturated fatty acids derivatives.

In a general manner, the methods of chemical synthesis are moreover not very selective, including many steps, very frequently need intermediate reactions for protecting some functions and require costly and/or toxic reagents. The European patent EP 0968 998 (Elf Atochem S.A) discloses a method of chemical synthesis of ceramides analogs, starting from an acylating agent and an amino-alcohol. This synthesis method however has the drawback of being very poorly selective, so that a molar yield lower than 75% is obtained. It has been mentioned that the steps of this synthesis may also be performed through enzymatic way and namely using classical esterases, particularly lipases and proteases, without precising their performance or any advantage resulting from this way.

The biotechnological way using enzymatic synthesis of the ceramide-type compounds has indeed been widely explored: in international patent WO 94/26919 to Gist Brocades (1997) has been described a synthesis method using a lipase of *Pseudomonas alcaligenes* to achieve the amide bond between phytosphingosine and methyl stearate. However, this reaction necessitates a very precise solvent, preferably tetrahydrofuran (THF). From this fact, such a way of synthesis is very costly and then poorly appropriate to industrial use.

Other publications disclose the use of lipases for the production of amide bonds in an organic solvent, namely Zalks A. et. al.'s (*Proc. Natl. Acad. Sci. U.S.A.* (1985) 82; 3192-3196) and Margolin A. C. et al.'s (*J. Am. Chem. Soc.* (1987) 109; 3802-3804). However, according to these studies, the amidation reaction of the lysosphingolipids, the amino-alcohol class needed for the synthesis of ceramides, appears to be unfruitful whatever the nature of the lipase is. The use of lipases on reactants having several functional groups such as amino-alcohols, has also been reported in literature. Several factors are able to greatly influence the formation of products, namely the type of lipase, the type of substrate and also the type of used solvent.

Studies performed by Bisfline R. G. et. al. (*JAOCS*, 1991, 68, 95-98) as well as by Djeghaba Z. et. al. (*Tetrahedron Lett.* 1991, 32; 761-762) have on their side evidenced the fact that the solvent nature may influence the activity and the selectivity of the enzyme during amidation reactions. Similarly, Montet D. et. al. (Revue Frangaise des Corps Gras (1989) 36; 79-83) have shown that, during the acylation reaction of amino propanol by the *Mucor michei* lipase in an organic solvent, selectivity is strongly influenced by the solvent nature. It has to be noticed that the use of this lipase did not allow to carry out the amidation reaction of lysosphingolipid. Not all the lipases are actually able to achieve the amide bond needed for the synthesis of ceramides. This has been namely set forth in another publication from Montet D. et. al. (*Fat Sci. Technol.* 1989, 91; 14-18). Another disclosure in European patent EP 0298796 (Graille J. et. al.) also mentions this result and discloses a method allowing the performance of an amidation, namely with the *Mucor michei* enzyme. Despite very precise conditions, the yields obtained for this conversion remain very variable, as evidenced by the performed tests and with a maximum of about 80% conversion. Such yields are insufficient to allow a fruitful exploitation of these enzymatic reactions.

Accordingly, none of the methods previously set forth in the prior art has until now led to the synthesis of ceramide-type compounds in a satisfactory manner. Yet, such compounds are highly interesting for the amphiphile industry in general, in such various domains as the tensio-active agents, wetting agents, anti-corrosive agents and so on. These molecules may find applications such as in industry, house-care, cosmetics as pharmaceutics. There was then a practical and permanent need to find a method of synthesis of ceramide-type compounds, which would be at the same time easy, effective, economical and consistent with the industrial conditions.

This industrial problem has been solved in a particularly surprising manner, according to the present invention, using a synthesis method including at least a step of amide formation performed by means of the *Candida Antartica* lipase B, and a step of esterification, similarly achieved using a lipase-type enzyme.

Unlike prior art, such a method is noticeable in the fact it includes only two steps, simple and fast, which do not require either a solvent or a purification and will be performed with a quantitative yield for each of these two steps.

Moreover, the use of enzymes leads to a very significant selectivity for the desired product. This method thus constitutes a solution to the difficulties encountered until now for the synthesis of ceramide-type compounds.

This invention has for an object a method of synthesizing ceramide-type compounds, including at least a step of amide formation performed by means of the *Candida Antartica* lipase B, and a step of esterification, also achieved using lipase-type enzyme, the said compounds of ceramide type having the general formula (I):

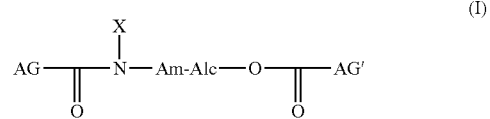

wherein the group Am-Alc figures a C2 to C6 carbon chain, preferably saturated, linear or optionally branched, stemming from an amino-alcohol; X figures a hydrogen atom or a C1 to C4 carbon chain, optionally hydroxylated on the 2' and/or following positions of the amino group; and in which each of the groups AG and AG' figures a C4 to C30 carbon chain, saturated or unsaturated, stemming from a fatty acid or a fatty acid ester; the two groups AG and AG' may be identical or different.

The ceramide-type compounds obtained according to this invention constitute a defined category of pseudo-ceramides. By pseudo-ceramides is generally understood compounds having an amide function and another bond. According to this invention, the pseudo-ceramides of formula (I) distinguish themselves by the fact that the supplementary bond is of the ester type. This ester bond is specially oriented in the molecule. In this manner, these pseudo-ceramide-type compounds are noticeably close to the natural ceramides or to pseudo-ceramides stemming from chemical synthesis. Due to the fact that their chemical group are similar, they often show the same properties.

By quantitative yield is understood a yield higher than 93%. A yield of almost 100% is even obtained during the amide formation step.

The two steps, more widely disclosed hereinafter, are independent and may be performed successively and/or simultaneously, in a different order without this having any consequence on the structure of the synthesized product.

According to this invention, it is understood as amide formation step, the step consisting in reacting an amino-alcohol with a fatty acid and/or an ester of a fatty acid. The first step may be pictured by the following reaction scheme (A) leading to the production of intermediary compounds of formula (II).

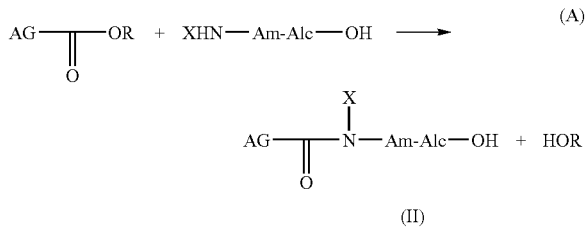

According to the invention, R is a hydrogen atom or a carbon chain including from 1 to 5 carbon atoms such as, namely, a methyl, ethyl, propyl, butyl, pentyl group, optionally substituted such as a glyceryl group (trihydroxypropane). However, R may also be any chemical group as far as it does not induce any sterical hindrance which may impede the accessibility to the carboxyl function of the fatty acid or of the fatty acid ester. Moreover, R will be preferably selected in such a manner that the alcohol ROH will be volatile, such as ethanol or isopropanol. Otherwise, a step of purification will be necessary and may be performed using HPLC (high performance liquid chromatography) chromatography on a column loaded with silica or by crystallisation.

This amidation step achieves the amide bond between the carbonyl function of a fatty acid or the corresponding ester and the primary or secondary amine function of an amino alcohol or an ester of an amino alcohol, by means of a lipase-type enzyme. More particularly is used a lipase B from *Candida Antartica*, belonging to the classes of the triacylglycerolhydrolases and of the carboxylesterases (enzymatic class EC 3.1.1.3). It may mainly matter of the lipase marketed by the company Novozymes S.A. under the trade name Novozym® 435, produced by culturing the genetically modified micro organism *Aspergillus Oryzae* and advantageously immobilised on a carrier.

The performance is not restricted to the use of the enzymes presently marketed by this company. However, it is to be noted that this type of lipase has to be used to obtain good yields according to the invention.

Preferably, the amidation reagents will be used in stoechiometric conditions in order that, in these proportion, all the reagents are consumed, avoiding residues.

By esterification step will be understood the reaction through which a fatty acid or a fatty acid ester is grafted on the free alcohol function, terminal or not, of an amino-alcohol. In the case of this step follows the amidation step, it may be pictured by the following reaction scheme (E):

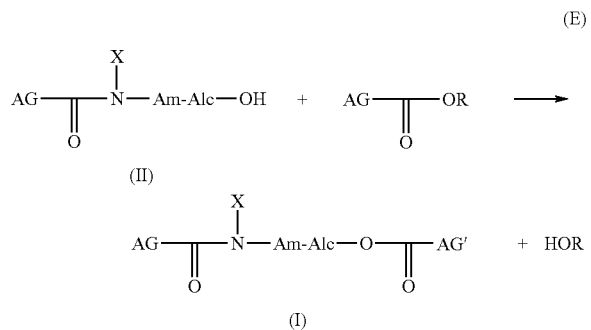

According to the invention, R is a hydrogen atom or a carbon chain including from 1 to 5 carbon atoms such as, namely, a methyl, ethyl, propyl, butyl, isobutyl, tertbutyl, pentyl, isopentyl, optionally substituted such as a glyceryl group (trihydroxypropane) or a trimethyloxypropyl group. However, R may also be any chemical group as far as it does not induce any sterical hindrance which may impede the accessibility to the carboxyl function of the fatty acid or of the fatty acid ester. Moreover, as for the amidation, R will be preferably selected in such a manner that the alcohol ROH will be volatile, such as ethanol or isopropanol. Otherwise, a step of purification will be necessary and may be performed, for example, by distillation.

This esterification step achieves the ester bond between the hydroxyl group of the compound of formula (II) (amide-alcohol) and the carboxyl group of the fatty acid or fatty acid ester, saturated or unsaturated, by means of a lipase-type enzyme and more particularly of a lipase belonging to the class of the triacylglycerolhydrolases (Enzymatic class EC 3.1.1.3.).

During this step may be used, un a more general manner, any enzyme able to specifically catalyse this ester-bond reactions. However is particularly preferred the *Rhizomucor miehei* lipase. It also has been discovered that this enzyme does not require solvent and, due to its specificity, has the advantage of performing the ester formation with a very good yield. It also contributes to the improvement of the global yield of the pseudo-ceramide synthesis according to the present invention.

Particularly, without being limitative, may be used the lipase marketed by the company Novozymes SA under the trade name Lipozyme® RM IM, also produced by culturing the genetically modified micro-organism *Aspergillus Oryzae* and advantageously immobilised on a carrier.

According to a particularly interesting embodiment of the process, the lipase B from *Candida Antartica* is used for the amidation step and the *Rhizomucor miehei* lipase is used for the esterification step. These two enzymes are indeed highly selective. Novozym® 435 preforms the amidation step only and Lipozyme® RM IM the esterification step only. It is noticeable that the order of the steps involving these two enzymes may be inverted without affecting the nature of the product and with a similar yield.

Moreover, these two steps may be carried out simultaneously. If only one kind of fatty acid is used, the chains AG and AG' being identical, only one ceramide-type compound of formula (I) will be obtained, including two identical AG and AG' groups. On the other hand, when two ore more fatty acids are used, a mixture of ceramide-type compounds will be obtained, all of them of formula (I) but containing the various possible combinations of AG and AG' groups.

In each of these reaction are advantageously used lipases immobilized on an inert organic carrier, which allows them to be easily removed from the reaction medium and to be then recycled. Preferably, they will be adsorbed on a macroporous resin, such as Novozym® 435 and Lipozyme® RM IM are. The cost of this process is in fact very advantageously reduced by recycling the enzyme. It has thus been observed that Novozym® 435 may be recycled about 10 times without loss of activity in the amidation reaction according to this process.

More precisely, the synthesis method according to the invention may be preferably achieved in the following manner:

the amide formation step occurs by mixing, in stoechiometric conditions, the fatty acid or the corresponding ester with an amino-alcohol, in the presence of a lipase such as Novozym® 435. The reaction is carried out at a temperature comprised between 40 and 100° C., preferably between 55 and 85° C. It may occur under atmospheric pressure or under a reduced pressure comprised between 1 and 500 mbars, preferably between 30 and 200 mbars. In order to reach a quantitative yield of at least about 93% in these conditions, the reaction is carried on during at least 16 hours, preferably during at least 20 hours.

the esterification step is carried out by reacting the amide obtained at first step with a fatty acid or the corresponding ester, in the presence of a lipase such as Lipozyme® RM IM. The ratio fatty acid ester/amido alcohol is comprised between 1 and 2, preferably between 1 and 1.5. The reaction is carried out at a temperature comprised between 40 and 100° C., preferably between 50 and 70° C. It may occur under atmospheric pressure or under a reduced pressure comprised between 1 and 500 mbars, preferably between 30 and 200 mbars. In order to reach a quantitative yield of at least about 93% in these conditions, the reaction is carried on during at least 18 hours, preferably during at least 24 hours.

Advantageously, each step is carried out under a reduced pressure comprised between 30 and 200 mbars. It has indeed occurred that the reduced pressure leads to the removing of water or alcohol forming progressively during condensation, and thus significantly accelerates the kinetic of the reaction. Moreover, the reduced pressure limits the degradation of numerous oxidizable fatty acids.

For the above related reasons, it must been insisted on the fact that the order of sequencing of these two reactions with these two enzymes is only given as an example and is not to be considered as limitative. It is left to the experimenter's initiative.

Thus, according to an achievement variant, the synthesis may be carried out according to a first esterification step, which may be pictured by the following reaction scheme (E'):

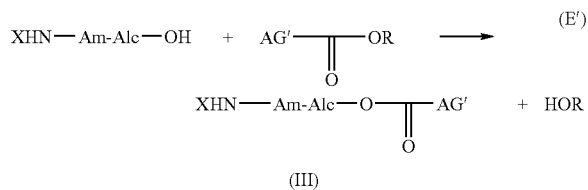

This esterification step occurs between an amino-alcohol and a fatty acid or a fatty acid ester to obtain an amino-ester of fatty acid, in the previously described, esterification-favourable conditions of reaction (E).

The second step will be the amide formation step, which may be pictured by the following reaction scheme (A'):

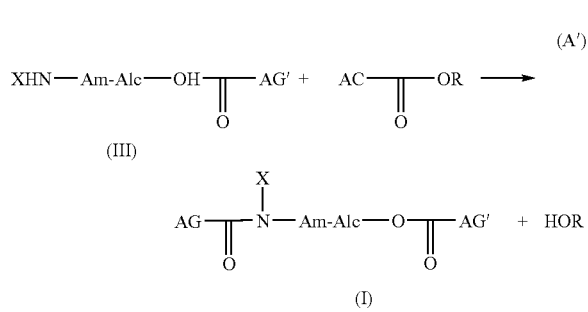

This second synthesis step is carried out between the amino-ester of fatty acid previously obtained and a fatty acid or a fatty acid ester in the previously described conditions of reaction (A).

When using the *Candida antartica* lipase B and the *Rhizomucor miehei* lipase, no solvent is needed in any of the steps of the pseudo-ceramide synthesis. At a temperature above around 65° C. in each reaction, the reagents and the products are indeed on liquid form, which allows them to play the role of solvent. This allows advantageously to avoid a purification step for the compounds (I) thus formed.

It is noticeable that the compounds of formula (I) are obtained in the form of a mixture with residual fatty acids or fatty acid esters, such as ethyl palmitate. This residual compound is not a drawback for formulations such as cosmetic or dermatological compositions. However, if necessary, the compound of formula (I) may be purified according to usual separation methods, such as HPLC or chromatography on silica or cellulose, or by crystallisation.

The process according to the invention thus comprises advantageously a restricted number of steps, at least one or two (amidation and esterification, simultaneously or successively). The compounds of formula (I) being particularly stable, other steps may however be added, especially after the amidation and esterification steps, such as formation of alkylated, oxydized or reduced derivatives.

In the case when solvents such as tert-butyl ether (TBEE) or hexane are wished to be used, the reaction will be carried out at atmospheric pressure.

The highest reaction temperatures are determined by the recycling capacity of the enzymes. In general, the person skilled in the art will understand that the synthesis conditions may vary depending on several factors, mainly the concentration in enzymes, pH, temperature. For each step, it will be tried to reach the optimal enzyme activity conditions. As an example, without being limitative, one may refer to the processes described in examples 1 to 21.

The continuation of each reaction beyond the time displayed in the previously described conditions is not harmful, but does not necessarily lead to a yield improvement.

The fatty acids or fatty acid esters which may be used according to the invention have a AG or AG° C4 to C30 carbon chain, preferably linear, saturated or unsaturated, optionally hydroxylated. Preferably will be selected those constituted by 10 to 22 carbon atoms. Moreover, the fatty acids are preferably not hydroxylated in alpha of the C=O group, in order to avoid parallel acylations, especially during esterification.

As examples of fatty acids may be cited:
capric acid (decanoic acid)
undecanoic acid
lauric acid (dodecanoic acid)
myristic acid (tetradecanoic acid)
palmitic acid (hexadecanoic acid)
stearic acid (octadecanoic acid)
oleic acid (octadeca-9-enoic acid)
ricinoleic acid (12-hydroxy-octadeca-9-enoic acid)
linoleic acid (octadeca-9,12-dienoic acid)
linolenic acid (α: octadeca-9,12,15-trienoic acid or γ: octadeca-6,9,12-trienoic acid)
eicosapentaenoic acid (eicosa-5,8,11,14,17-pentaenoic acid)
docosahexaenoic acid (docosa-4,7,10,13,16,19-hexaenoic acid)
stearidonic acid (octadeca-6,9,12,15-tetraenoic acid)
aleuritolic acid (9,10,16-trihydroxy hexadecanoic acid)

Among the fatty acid esters which may be used may be cited the methyl, ethyl, propyl, isopropyl, terbutyl . . . esters. The phosphorylated derivatives such as some sphingosine derivatives are on the other hand excluded.

The fatty acids or fatty acid esters may be used in pure form or in form of a mixture of fatty acids, especially extracted from microalgae such as spirulin, from vegetal oils such as evening primrose oil, borage oil, or from animal oils such as fish oils. It especially may be a mixture of fatty acids obtained by oil saponification.

The amino-alcohols which may be used according to the present invention include one or several primary or secondary hydroxyl groups. The amine function may be primary or secondary. In order to optimise the yield will be preferably used an amino-alcohol including a primary amine function.

The amino-alcohols which may be used according to the present invention correspond to the general formula (IV):

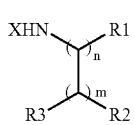 (IV)

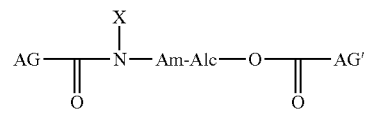 (I)

in which:
n is an integer selected from the numbers 1, 2, 3 and m is an integer selected from the numbers 1, 2, 3,
X is selected from the group composed of hydrogen and a C1 to C4 carbon chain, optionally hydroxylated on the positions 2' and/or followings of the amino group;
R1 is selected from the group composed of hydrogen and a C1 to C4 carbon chain, preferably saturated, linear, optionally branched and/or hydroxylated,
R2 is selected from the group composed of hydrogen, —OH, NH$_2$ and a C1 to C4 carbon chain, preferably saturated, linear, optionally branched and/or hydroxylated,
R3 is selected from the group composed of hydrogen, —OH and —CH$_2$OH,
and in which at least one of the groups R1, R2 or R3 includes a —OH group.

This process, due to the use of very selective enzymes, shows the advantage of permitting the synthesis of ceramide-type compounds of formula (I) with a very good yield, including the case when the amino-alcohol includes only one hydroxyl group. Thus, preferably, only one of the groups R1, R2 and R3 includes a —OH function.

The amino-alcohols are linear, optionally branched and contain from 2 to 6 carbon atoms. Preferably, they are partially soluble into the starting fatty acid or fatty acid ester.

As examples of amino-alcohols may be cited:
1-amino-2-propanol
2-amino-1-propanol
3-amino-1-propanol
2-(methylamino)ethanol
1-amino-2-butanol
2-amino-1-butanol
3-amino-1-butanol
4-amino-1-butanol
2-amino-2-methyl-1-propanol
2-(ethylamino)ethanol
2-amino-3-methyl-1-butanol
1-amino-2-pentanol
2-amino-1-pentanol
5-amino-1-pentanol
2-(propylamino)ethanol
1-amino-2-hexanol
2-amino-1-hexanol
6-amino-1-hexanol
diethanolamine
3-amino-1,2-propanediol
2-amino-1,3-propanediol
2-amino-2-methyl-1,3-propanediol
2-amino-2-ethyl-1,3-propanediol
2-amino-2-hydroxymethyl-1,3-propanediol
N-2,3,4,5,6-pentahydroxyhexylamine The ceramide-type compounds directly obtained by the above-said process of synthesis according to the invention have the general structure (I):

in which the group Am-Alc figures a C2 to C6 carbon chain, preferably saturated, linear or optionally branched, obtained from an amino-alcohol; X figures a hydrogen atom or a C1 to C4 carbon chain, optionally hydroxylated on the 2' and/or following positions of the amino group; and in which each of the groups AG and AG' figures a C4 to C30 carbon chain, saturated or unsaturated, obtained from a fatty acid or a fatty acid ester; the two groups AG and AG' may be identical or different.

These compounds of formula (I) thus necessarily include two oxy groups, separated by at least one amide bond and one ester bond and by the carbon chain Am-Alc. They further include two carbon chains AG and AG' which may be identical or different, depending of the fatty acid and/or the fatty acid ester used as reagents.

The compounds of formula (I) have a melting point around 60-65° C., which allows them to be synthesized at high temperatures and to be easily incorporated into formulations. These compounds have besides good preservation properties, better than those of the corresponding amide compounds of formula (II).

The process may be used on optically active compounds. This selectivity is indeed preserved in the final compound (I). When they have at least one asymmetric carbon, these new compounds may be resolved into their isomers or their erythro or threo diastereomers.

Among the novel ceramide-type compounds according to the invention may be cited, without limitation, as preferred compounds:
(3-decanoyloxy)-2-hydroxy propyl amide of octadeca-9,12-cis-cis-dienoic acid
(3-dodecanoyloxy)-2-hydroxy propyl amide of octadeca-9,12-cis-cis-dienoic acid
(3-tetradecanoyloxy)-2-hydroxy propyl amide of octadeca-9,12-cis-cis-dienoic acid
(3-hexadecanoyloxy)-2-hydroxy propyl amide of octadeca-9,12-cis-cis-dienoic acid
(3-octadecanoyloxy)-2-hydroxy propyl amide of octadeca-9,12-cis-cis-dienoic acid
(3-octadeca-9-dienoyloxy)-2-hydroxy propyl amide of octadeca-9,12-cis-cis-dienoic acid
(3-octadeca-9,12-cis-cis-dienoyloxy)-2-hydroxy propyl amide of octadeca-9,12-cis-cis-dienoic acid
(3-octadeca-12-hydroxy-9 dienoyloxy)-2-hydroxy propyl amide of octadeca-9,12-cis-cis-dienoic acid
(3-eicosa-5,8,11,14,17-pentaenoyloxy)-2-hydroxy propyl amide of octadeca-9,12-cis-cis-dienoic acid
(3-docosa-4,7,10,16,19-hexaenoyloxy)-2-hydroxy propyl amide of octadeca-9,12-cis-cis-dienoic acid When the amidation step of the above described process is the first step of synthesis, the obtained intermediary amides have the general formula (II):

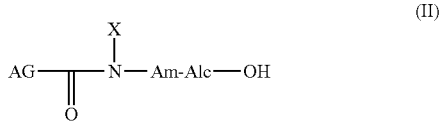

(II)

in which the group Am-Alc figures a C2 to C6 carbon chain, preferably saturated, linear or optionally branched, obtained from an amino-alcohol; X figures a hydrogen atom or a C1 to C4 carbon chain, optionally hydroxylated on the 2' and/or following positions of the amino group; and in which the group AG figures a C4 to C30 carbon chain, saturated or unsaturated, obtained from a fatty acid.

These intermediary compounds are obtained by amidation of the carboxyl group of the fatty acids and/or the fatty acid esters by the amine function of the amino-alcohols according to the reaction scheme (A) of the process of the present invention. This step is performed by means of the *Candida antartica* lipase B in the previously described conditions.

These intermediaries are particularly interesting by the fact that they lead to the novel ceramide-type compounds in a single esterification step (E) described according to the present invention.

Such amide intermediaries however degrade quickly. It is therefore appropriate to carry out the esterification reaction without delay, leading to much more stable pseudo-ceramides (I).

Among these new intermediary compounds of formula (II) may be cited as examples:

(2-hydroxy-propyl) amide of octadeca-9,12-cis-cis-dienoic acid
(1-hydroxymethyl-propyl) amide of octadeca-9,12-cis-cis-dienoic acid
(2,3-dihydroxy-propyl) amide of octadeca-9,12-cis-cis-dienoic acid
(2,3-dihydroxy-propyl) amide of decanoic acid
(2,3-dihydroxy-propyl) amide of dodecanoic acid
(2,3-dihydroxy-propyl) amide of tetradecanoic acid
(2,3-dihydroxy-propyl) amide of hexadecanoic acid
(2,3-dihydroxy-propyl) amide of octadecanoic acid
(2,3-dihydroxy-propyl) amide of octadec-9-cis-enoic acid
(2,3-dihydroxy-propyl) amide of octadeca-9,12-cis-cis-dienoic acid
(2,3-dihydroxy-propyl) amide of 12-hydroxy-octadec-9-enoic acid The examples 1 to 11 describe more precisely the amidation reaction conditions.

When the esterification step of the above described process is the first step of synthesis, the obtained intermediary amides have the general formula (III):

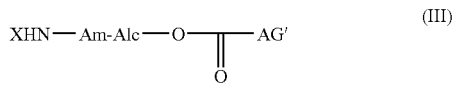

(III)

in which the group Am-Alc figures a C2 to C6 carbon chain, preferably saturated, linear or optionally branched, obtained from an amino-alcohol; X figures a hydrogen atom or a C1 to C4 carbon chain, optionally hydroxylated on the 2' and/or following positions of the amino group; and in which the group AG' figures a C4 to C30 carbon chain, saturated or unsaturated, stemmed from a fatty acid.

These intermediary compounds are obtained by esterification of the carboxyl group of the fatty acids and/or the fatty acid esters by the hydroxyl group of the amino-alcohols according to the reaction scheme (E) of the process of the present invention. This step is performed by means of the *Rhizomucor miehei* lipase in the previously described conditions.

These intermediaries are particularly interesting by the fact that they lead to the novel ceramide-type compounds in a single amidation step (A) described according to the present invention.

Among these new intermediary compounds of formula (III) may be cited as examples:

1-amino-2-hydroxy propyl ester of decanoic acid
1-amino-2-hydroxy propyl ester of dodecanoic acid
1-amino-2-hydroxy propyl ester of tetradecanoic acid
1-amino-2-hydroxy propyl ester of hexadecanoic acid
1-amino-2-hydroxy propyl ester of octadecanoic acid
1-amino-2-hydroxy propyl ester of octadec-9-cis-enoic acid
1-amino-2-hydroxy propyl ester of octadeca-9,12-cis-cis-dienoic acid
1-amino-2-hydroxy propyl ester of 12-hydroxy-octadec-9-enoic acid
1-amino-2-hydroxy propyl ester of eicosa-5,8,11,14,17-pentaenoic acid
1-amino-2-hydroxy propyl ester of docosa-4,7,10,16,19-pentaenoic acid The ceramide-type compounds of formula (I) may be used as active ingredients in cosmetic and/or pharmaceutical compositions, more precisely in the dermatological compositions. These compositions may contain from 0.01 to 90% of the said compounds, preferably from 0.1 to 30% w/total w. and more preferably from 0.1 to 5%. Such compositions may include the usual cosmetically acceptable vehicles, such as diluents, dispersing agents, gelling agents, carriers for ceramides, solid softening agents, gums, resins, tensioactive agents, solvents, charges such as rice starch, pigments, preservatives, essential oils, antioxidants, colorants, mother-of-pearls, perfumes, odour absorbing agents, pH regulators or neutralizing agents, viscosifying agents, such as those usually used.

The compositions are presented in a forma suitable for skin and integument application, such as a gel, lotion, especially capillary lotion and varnish, emulsion or dispersion, especially of O/W or W/O type, cream, especially mascara cream, unguent, milk, foam, sticks, especially lip balms and lipsticks.

The compounds obtained by the process according to the invention may be formulated in a similar way than those described in the prior art. Without being limitative, it may be useful to revert to the provided examples of formulation.

In the form of an emulsion, the composition according to the inventions contains emulsifiers and coemulsifiers such as those used by the people skilled in the art. Example of suitable emulsifiers and coemulsifiers are fatty acid and polyol esters such as glyceryl stearate, fatty acid and polyethyleneglycol esters such as PEG-20 stearate. Advantageously, the emulsifier and coemulsifier concentration is comprised between 0.3 and 30% w/w, preferably between 0.5 and 5%.

These compositions are thus useful for the care and/or treatment and/or protection of human and/or animal epidermis and/or its formations (hairs, nails . . . ). Restoring the cutaneous lipidic balance, they indeed restore the cutaneous layer alterations and control the loss of water. They are thus particularly useful to prevent and/or solve skin problems such as dryness, wrinkles and cutaneous folds, desquamation, cracks and fissures, to maintain a soft, smooth, hydrated and elastic skin, and to counteract the skin ageing signs. The cosmetic or dermatological compositions neither display any toxicity or local intolerance, nor are they allergenic.

The following examples are presented to illustrate the invention and are not in any case to be considered as a limit to the scope of the invention. Apart from other indications, the concentrations are given in percentage related to the global weight of the composition.

In the following examples, the amidation reaction is performed by means of the *Candida antartica* lipase B immobilized on an inert support, used in the form of the product marketed by the firm Novozymes S.A. under the trade name Novozym® 435. This compound is thermostable and displays an optimal activity at 40-60° C. It has on the other hand a declared esterification activity of 10.000 Propyl Laurate Unit per gram (PLU/g).

The esterification reaction is performed by means of the *Rhizomucor miehei* lipase immobilized on an inert support, used in the form of the product marketed by the firm Novozymes S.A. under the trade name Lipozyme® RM IM. This compound displays an optimal activity at 30-70° C. and has an activity of about 150 IUN/g.

I. Examples of Amidation Reaction From Different Aminoalcohols (1-amino-2-propanol, 2-amino-1-butanol and 3-amino-1,2-propanediol) in the Presence of Fatty Acids, Especially Linoleic Acid

EXAMPLE 1

Synthesis of the (2-hydroxy-propyl) amide of octadeca-9,12-cis-cis-dienoic acid

In a 500 mL flask were poured 75.11 g of 1-amino-2-propanol (1 mole) and 280.24 g of linoleic acid (1 mole). The mixture was heated under stirring up to 65° C. before adding 5 g of Novozym® 435. The reaction medium was then put under reduced pressure (50 mbars) to eliminate the forming water.

After 20 hours of reaction, the enzyme on solid phase was removed through filtration. The conversion of linoleic acid into amide was above 95%. The obtained product was a beige-coloured wax.

The obtained product was analysed through High Performance liquid Chromatography (HPLC) according to the usual method and along the following conditions:

Column Nucleosil 100 $C_{18}$ 5 μm (250×2 mm)

Gradient:

| Time (minutes) | Methanol (%) | Water (%) |
|---|---|---|
| 0 | 85 | 15 |
| 10 | 85 | 15 |
| 20 | 100 | 0 |
| 40 | 100 | 0 |
| 45 | 85 | 15 |

Flow: 0.22 ml.mn$^{-1}$.

Detection: Ultraviolet λ=210 nm.

HPLC retention time of the product: 11.98 minutes

Example 1
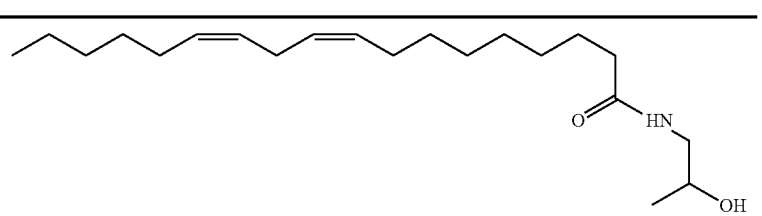

Example 2
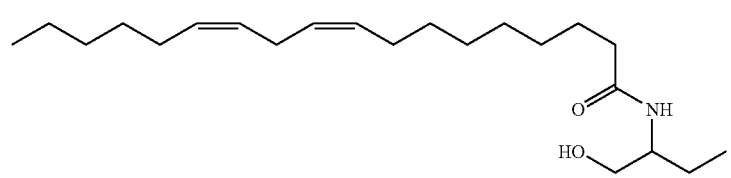

Example 3
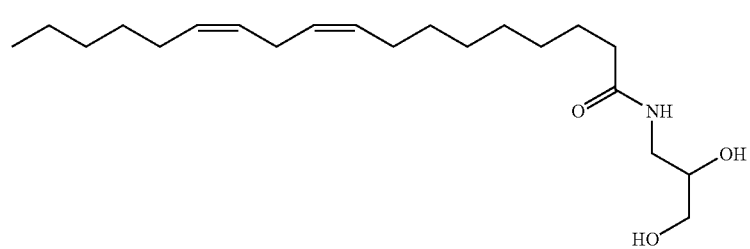

EXAMPLE 2

Synthesis of the (1-hydroxymethyl-propyl)amide of octadeca-9,12-cis-dienoic acid In a 500 mL flask were poured 89.11 g of 2-amino-1-butanol (1 mole) and 280.24 g of linoleic acid (1 mole). The mixture was heated under stirring up to 65° C. before adding 5 g of Novozym® 435. The reaction medium was then put under reduced pressure (50 mbars) to eliminate the forming water.

After 20 hours of reaction, the enzyme on solid phase was removed through filtration. The conversion of linoleic acid into amide was above 95%. The obtained product was a beige-coloured wax.

HPLC retention time of the product: 13.20 minutes

EXAMPLE 3

Synthesis of the (2,3-dihydroxy-propyl) amide of octadeca-9,12-cis-cis-dienoic acid In a 500 mL flask were poured 91.11 g of 3-amino-1,2-propanediol (1 mole) and 280.24 g of linoleic acid (1 mole). The mixture was heated under stirring up to 65° C. before adding 5 g of Novozym® 435. The reaction medium was then put under reduced pressure (50 mbars) to eliminate the forming water.

After 20 hours of reaction, the enzyme on solid phase was removed through filtration. The conversion of linoleic acid into amide was above 95%. The obtained product was a beige-coloured wax.

HPLC retention time of the product: 10.65 minutes

IR (ν, cm$^{-1}$, CH$_2$Cl$_2$): 3300, 2900, 2850, 1630, 1545, 1465.

II. Examples of Amide Syntheses From Different Fatty Acid Esters in the Presence of 3-amino-1,2-propanediol.

Example 4

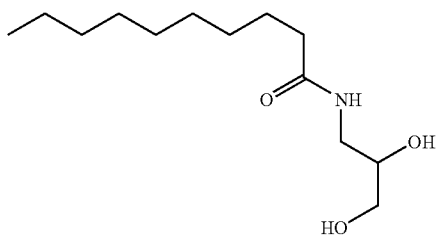

Example 5

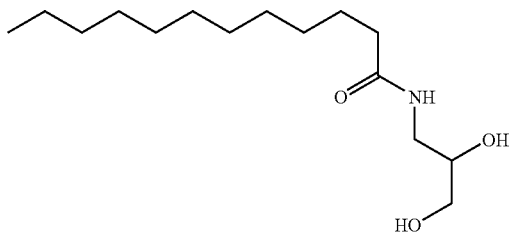

Example 6

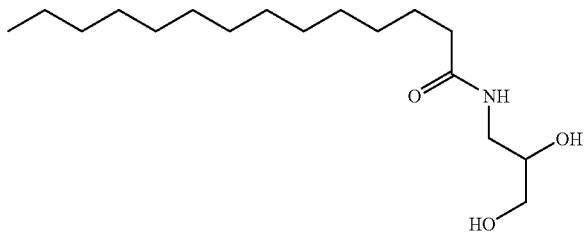

Example 7

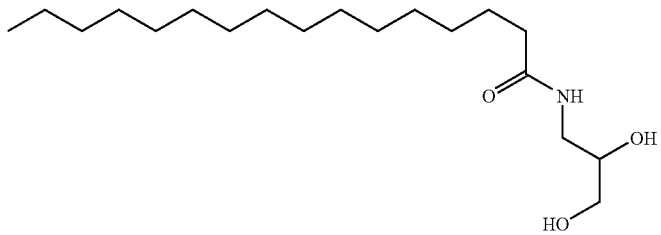

-continued

Example 8
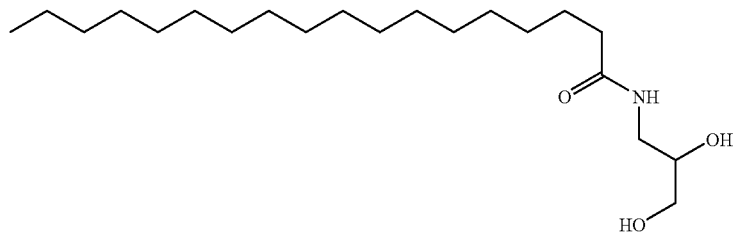

Example 9
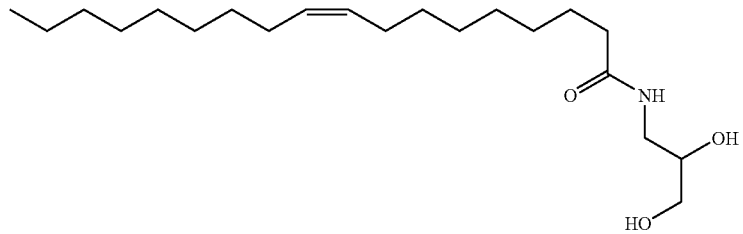

Example 10
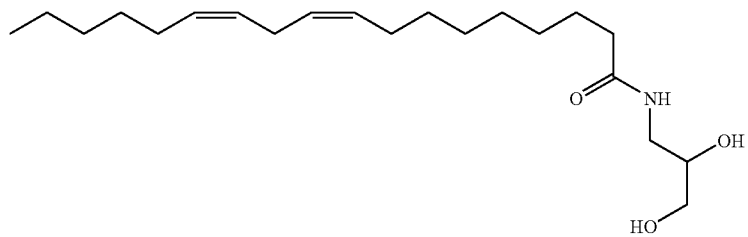

Example 11
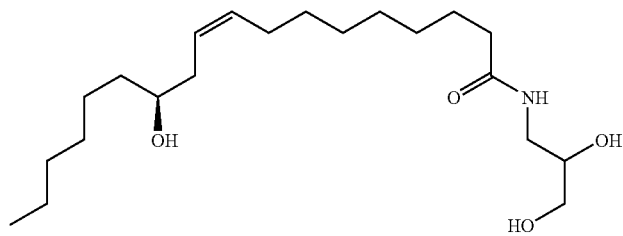

EXAMPLE 4

Synthesis of the (2,3-dihydroxy-propyl)amide of decanoic acid

In a 500 mL flask were poured 91.11 g of 3-amino-1,2-propanediol (1 mole) and 200.32 g of ethyl decanoate (1 mole). The mixture was heated under stirring up to 65° C. before adding 5 g of Novozym® 435. The reaction medium was then put under reduced pressure (50 mbars) to eliminate the forming ethanol.

After 24 hours of reaction, the enzyme on solid phase was removed through filtration. The conversion of ester into amide was above 99%. The obtained product was a cream-coloured wax.

HPLC retention time of the product: 4.47 minutes

EXAMPLE 5

Synthesis of the (2,3-dihydroxy-propyl)amide of dodecanoic acid

In a 500 mL flask were poured 91.11 g of 3-amino-1,2-propanediol (1 mole) and 228.37 g of ethyl laurate (1 mole). The mixture was heated under stirring up to 65° C. before adding 5 g of Novozym® 435. The reaction medium was then put under reduced pressure (50 mbars) to eliminate the forming ethanol.

After 24 hours of reaction, the enzyme on solid phase was removed through filtration. The conversion of ester into amide was above 99%. The obtained product was a cream-coloured wax.

HPLC retention time of the product: 5.65 minutes

EXAMPLE 6

Synthesis of the (2,3-dihydroxy-propyl)amide of tetradecanoic acid

In a 500 mL flask were poured 91.11 g of 3-amino-1,2-propanediol (1 mole) and 256.42 g of ethyl myristate (1 mole). The mixture was heated under stirring up to 65° C. before adding 5 g of Novozym® 435. The reaction medium was then put under reduced pressure (50 mbars) to eliminate the forming ethanol.

After 24 hours of reaction, the enzyme on solid phase was removed through filtration. The conversion of ester into amide was above 99%. The obtained product was a cream-coloured wax.

HPLC retention time of the product: 8.06 minutes

EXAMPLE 7

Synthesis of the (2,3-dihydroxy-propyl)amide of hexadecanoic acid

In a 500 mL flask were poured 91.11 g of 3-amino-1,2-propanediol (1 mole) and 284.48 g of ethyl palmitate (1 mole). The mixture was heated under stirring up to 65° C. before adding 5 g of Novozym® 435. The reaction medium was then put under reduced pressure (50 mbars) to eliminate the forming ethanol.

After 24 hours of reaction, the enzyme on solid phase was removed through filtration. The conversion of ester into amide was above 99%. The obtained product was a cream-coloured wax.

HPLC retention time of the product: 12.15 minutes

EXAMPLE 8

Synthesis of the (2,3-dihydroxy-propyl)amide of octadecanoic acid

In a 500 mL flask were poured 91.11 g of 3-amino-1,2-propanediol (1 mole) and 312.53 g of ethyl stearate (1 mole). The mixture was heated under stirring up to 65° C. before adding 5 g of Novozym® 435. The reaction medium was then put under reduced pressure (50 mbars) to eliminate the forming ethanol.

After 24 hours of reaction, the enzyme on solid phase was removed through filtration. The conversion of ester into amide was above 99%. The obtained product was a beige-coloured wax.

HPLC retention time of the product: 19.38 minutes

EXAMPLE 9

Synthesis of the (2,3-dihydroxy-propyl)amide of octadec-9-cis-enoic acid

In a 500 mL flask were poured 91.11 g of 3-amino-1,2-propanediol (1 mole) and 310.51 g of ethyl oleate (1 mole). The mixture was heated under stirring up to 65° C. before adding 5 g of Novozym® 435. The reaction medium was then put under reduced pressure (50 mbars) to eliminate the forming ethanol.

After 24 hours of reaction, the enzyme on solid phase was removed through filtration. The conversion of ester into amide was above 99%. The obtained product was a beige-coloured wax.

HPLC retention time of the product: 13.26 minutes

EXAMPLE 10

Synthesis of the (2,3-dihydroxy-propyl)amide of octadeca-9,12-cis-cis-dienoic acid In a 500 mL flask were poured 91.11 g of 3-amino-1,2-propanediol (1 mole) and 308.50 g of ethyl linoleate (1 mole). The mixture was heated under stirring up to 65° C. before adding 5 g of Novozym® 435. The reaction medium was then put under reduced pressure (50 mbars) to eliminate the forming ethanol.

After 24 hours of reaction, the enzyme on solid phase was removed through filtration. The conversion of ester into amide was above 99%. The obtained product was a beige-coloured wax.

HPLC retention time of the product: 10.37 minutes

IR (ν, cm$^{-1}$, CH$_2$Cl$_2$): 3300, 2900, 2850, 1630, 1545, 1465.

EXAMPLE 11

Synthesis of the (2,3-dihydroxy-propyl)amide of 12-hydroxy-octadec-9-enoic acid

In a 500 mL flask were poured 91.11 g of 3-amino-1,2-propanediol (1 mole) and 326.51 g of ethyl ricinoleate (1 mole). The mixture was heated under stirring up to 65° C. before adding 5 g of Novozym® 435. The reaction medium was then put under reduced pressure (50 mbars) to eliminate the forming ethanol.

After 24 hours of reaction, the enzyme on solid phase was removed through filtration. The conversion of ester into amide was above 99%. The obtained product was a beige-coloured wax.

HPLC retention time of the product: 5.34 minutes

III. Examples of Syntheses of the Ceramide-type Compounds by Reaction of a Fatty Acid Ester on the Amide Obtained by Condensation of Linoleic Acid on 3-amino 1,2-propanediol.

Example 12

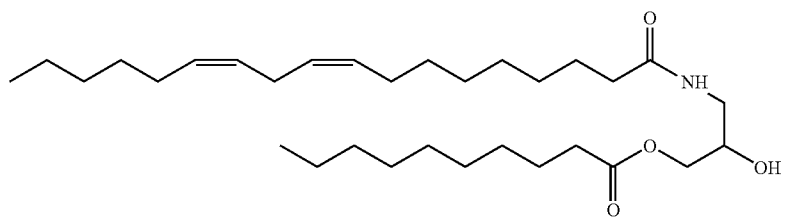

Example 13

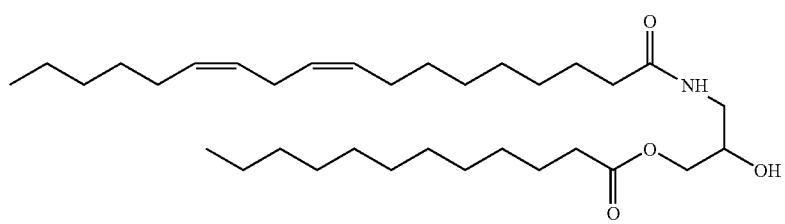

-continued
Example 14
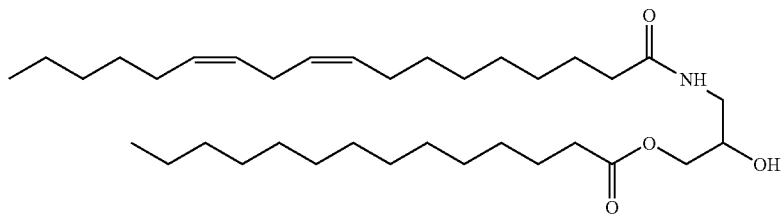
Example 15
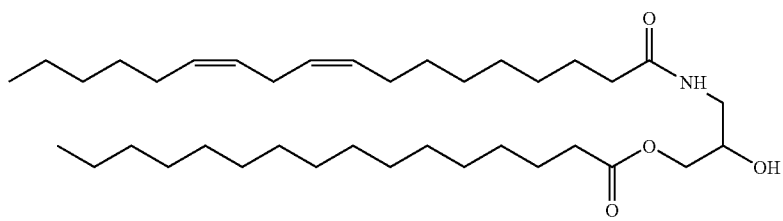
Example 16
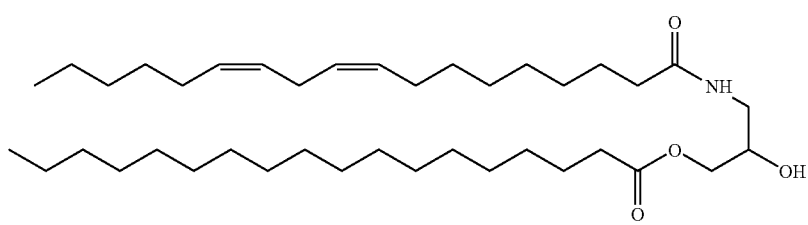
Example 17
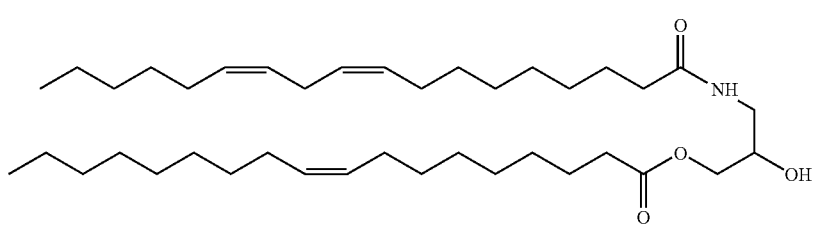
Example 18
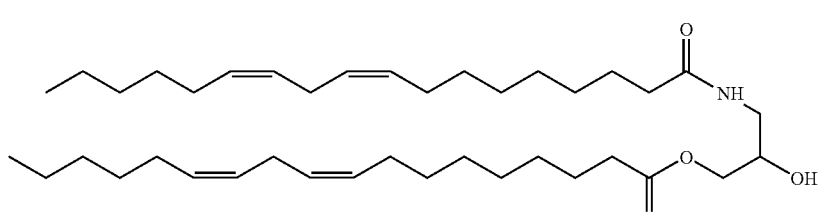
Example 19
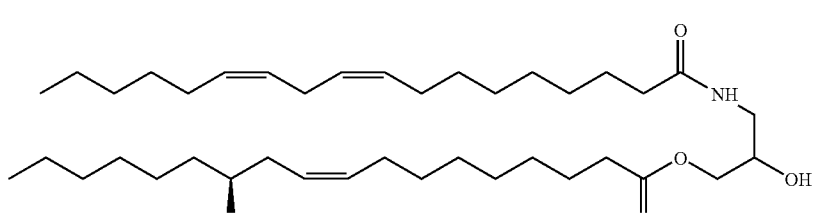
Example 20
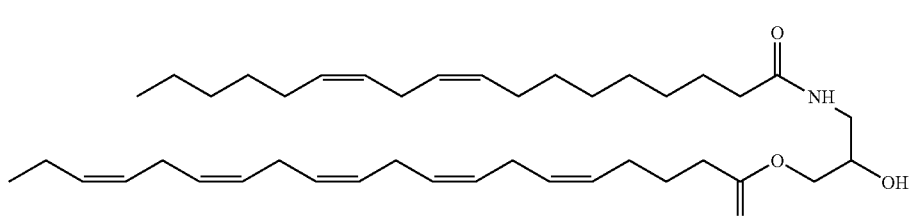

Example 21

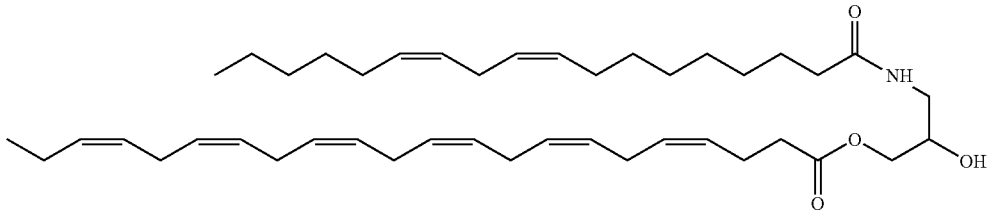

EXAMPLE 12

Synthesis of the (3-decanoyloxy)-2-hydroxypropyl amide of octadeca-9,12-cis-cis-dienoic acid In a 1.000 mL flask were poured 353.54 g of (2,3-dihydroxy-propyl) amide of octadeca-9,12-cis-cis-dienoic acid (1 mole) and 300.48 g of ethyl decanoate (1.5 mole). The mixture was heated under stirring up to 65° C. before adding 30 g of Lipozyme® RM IM. The reaction medium was then put under reduced pressure (50 mbars) to eliminate the forming ethanol.

After 24 hours of reaction, the enzyme on solid phase was removed through filtration. The conversion of the amide into N-decanoyl derivative was above 93%. The obtained product was a white wax.

HPLC retention time of the product: 25.35 minutes

EXAMPLE 13

Synthesis of the (3-dodecanoyloxy)-2-hydroxypropyl amide of octadeca-9,12-cis-cis-dienoic acid In a 1.000 mL flask were poured 353.54 g of (2,3-dihydroxy-propyl) amide of octadeca-9,12-cis-cis-dienoic acid (1 mole) and 342.55 g of ethyl laurate (1.5 mole). The mixture was heated under stirring up to 65° C. before adding 30 g of Lipozyme® RM IM. The reaction medium was then put under reduced pressure (50 mbars) to eliminate the forming ethanol.

After 24 hours of reaction, the enzyme on solid phase was removed through filtration. The conversion of the amide into N-dodecanoyl derivative was above 93%. The obtained product was a white wax.

HPLC retention time of the product: 27.28 minutes

EXAMPLE 14

Synthesis of the (3-tetradecanoyloxy)-2-hydroxypropyl amide of octadeca-9,12-cis-cis-dienoic acid In a 1.000 mL flask were poured 353.54 g of (2,3-dihydroxy-propyl) amide of octadeca-9,12-cis-cis-dienoic acid (1 mole) and 384.63 g of ethyl myristate (1.5 mole). The mixture was heated under stirring up to 65° C. before adding 30 g of Lipozyme® RM IM. The reaction medium was then put under reduced pressure (50 mbars) to eliminate the forming ethanol.

After 24 hours of reaction, the enzyme on solid phase was removed through filtration. The conversion of the amide into N-tetradecanoyl derivative was above 93%. The obtained product was a white wax.

HPLC retention time of the product: 28.93 minutes

EXAMPLE 15

Synthesis of the (3-hexadecanoyloxy)-2-hydroxypropyl amide of octadeca-9,12-cis-cis-dienoic acid In a 1.000 mL flask were poured 353.54 g of (2,3-dihydroxy-propyl) amide of octadeca-9,12-cis-cis-dienoic acid (1 mole) and 426.72 g of ethyl palmitate (1.5 mole). The mixture was heated under stirring up to 65° C. before adding 30 g of Lipozyme® RM IM. The reaction medium was then put under reduced pressure (50 mbars) to eliminate the forming ethanol.

After 24 hours of reaction, the enzyme on solid phase was removed through filtration. The conversion of the amide into N-hexadecanoyl derivative was above 93%. The obtained product was a white wax.

HPLC retention time of the product: 31.22 minutes

IR ($\nu$, $Cm^{-1}$, $CH_2Cl_2$): 3300, 2900, 2850, 1695, 1630, 1540, 1460.

EXAMPLE 16

Synthesis of the (3-octadecanoyloxy)-2-hydroxypropyl amide of octadeca-9,12-cis-cis-dienoic acid In a 1.000 mL flask were poured 353.54 g of (2,3-dihydroxy-propyl) amide of octadeca-9,12-cis-cis-dienoic acid (1 mole) and 468.79 g of ethyl stearate (1.5 mole). The mixture was heated under stirring up to 65° C. before adding 30 g of Lipozyme®D RM IM. The reaction medium was then put under reduced pressure (50 mbars) to eliminate the forming ethanol.

After 24 hours of reaction, the enzyme on solid phase was removed through filtration. The conversion of the amide into N-octadecanoyl derivative was above 93%. The obtained product was a white wax.

HPLC retention time of the product: 33.57 minutes

EXAMPLE 17

Synthesis of the (3-octadeca-9-enoyloxy)-2-hydroxypropyl amide of octadeca-9,12-cis-cis-dienoic acid In a 1.000 mL flask were poured 353.54 g of (2,3-dihydroxy-propyl) amide of octadeca-9,12-cis-cis-dienoic acid (1 mole) and 465.76 g of ethyl oleate (1.5 mole). The mixture was heated under stirring up to 65° C. before adding 30 g of Lipozyme® RM IM. The reaction medium was then put under reduced pressure (50 mbars) to eliminate the forming ethanol.

After 24 hours of reaction, the enzyme on solid phase was removed through filtration. The conversion of the amide was above 93%. The obtained product was a cream-coloured wax.

HPLC retention time of the product: 31.73 minutes

EXAMPLE 18

Synthesis of the (3-octadeca-9,12-cis-cis-dienoyloxy)-2-hydroxypropyl amide of octadeca-9,12-cis-cis-dienoic acid In a 1.000 mL flask were poured 353.54 g of (2,3-dihydroxy-propyl) amide of octadeca-9,12-cis-cis-dienoic acid (1 mole) and 462.76 g of ethyl linoleate (1.5 mole). The mixture was heated under stirring up to 65° C. before adding 30 g of Lipozyme® RM IM. The reaction medium was then put under reduced pressure (50 mbars) to eliminate the forming ethanol.

After 24 hours of reaction, the enzyme on solid phase was removed through filtration. The conversion of the amide was above 93%. The obtained product was a cream-coloured wax.

HPLC retention time of the product: 30.19 minutes

EXAMPLE 19

Synthesis of the (3-octadeca-12-hydroxy-9-dienoyloxy)-2-hydroxypropyl amide of octadeca-9,12-cis-cis-dienoic acid In a 1.000 mL flask were poured 353.54 g of (2,3-dihydroxy-propyl) amide of octadeca-9,12-cis-cis-dienoic acid (1 mole) and 489.76 g of ethyl ricinoleate (1.5 mole). The mixture was heated under stirring up to 65° C. before adding 30 g of Lipozyme® RM IM. The reaction medium was then put under reduced pressure (50 mbars) to eliminate the forming ethanol.

After 24 hours of reaction, the enzyme on solid phase was removed through filtration. The conversion of the amide was above 93%. The obtained product was a cream-coloured wax.

HPLC retention time of the product: 26.05 minutes

EXAMPLE 20

Synthesis of the (3-eicosa-5,8,11,14,17-pentaenoyloxy)-2-hydroxypropyl amide of octadeca-9,12-cis-cis-dienoic acid In a 1.000 mL flask were poured 353.54 g of (2,3-dihydroxy-propyl) amide of octadeca-9,12-cis-cis-dienoic acid (1 mole) and 495.75 g of ethyl 3-eicosa-5,8,11,14,17-pentaenoate (1.5 mole). The mixture was heated under stirring up to 65° C. before adding 30 g of Lipozyme® RM IM. The reaction medium was then put under reduced pressure (50 mbars) to eliminate the forming ethanol.

After 24 hours of reaction, the enzyme on solid phase was removed through filtration. The conversion of the amide was above 93%. The obtained product was a cream-coloured wax.

HPLC retention time of the product: 28.60 minutes

EXAMPLE 21

Synthesis of the (3-docosa-4,7,10,16,19-hexaenoyloxy)-2-hydroxypropyl amide of octadeca-9,12-cis-cis-dienoic acid In a 1.000 mL flask were poured 353.54 g of (2,3-dihydroxy-propyl) amide of octadeca-9,12-cis-cis-dienoic acid (1 mole) and 534.90 g of ethyl docosa-5,8,11,14,17-hexaenoate (1.5 mole). The mixture was heated under stirring up to 65° C. before adding 30 g of Lipozyme® RM IM. The reaction medium was then put under reduced pressure (50 mbars) to eliminate the forming ethanol.

After 24 hours of reaction, the enzyme on solid phase was removed through filtration. The conversion of the amide was above 93%. The obtained product was a cream-coloured wax.

HPLC retention time of the product: 29.37 minutes

IV. Examples of Cosmetic Compositions Including the Compounds of Formula I:

These preparations have been obtained by blending the ingredients.

In the examples and preparations, the indicated proportions are weight/total weight proportions.

| Emulsion-Cream oil-in-water | |
|---|---|
| Mineral oil | 4.00% |
| Ceramide-type compound of formula (I) | 0.10% |
| Ceteth 10 | 4.00% |
| Cetyl alcohol | 4.00% |
| Triethanolamine | 0.75% |
| Butane-1,3-diol | 3.00% |
| Xanthane gum | 0.30% |
| Preservative | 0.40% |
| Perfume | qs |
| Hydroxybutyl toluene | 0.01% |
| Water | qsp 100% |

| Lotion for dry hair | |
|---|---|
| Ceramide-type compound of formula (I) | 1.5% |
| Perfume | 0.10% |
| Hydroxyethyl cellulose | 0.40% |
| Absolute ethanol | 25.00% |
| p-Methylbenzoate - sodium hydroxide | 0.20% |
| Sterile demineralized water | qsp 100% |

| Moisturizing anti-ageing lotion for dry skin | |
|---|---|
| Ceramide-type compound of formula (I) | 1.5% |
| Perfume | 0.10% |
| Hydroxyethyl cellulose | 0.40% |
| Absolute ethanol | 25.00% |
| p-Methylbenzoate | 0.20% |
| Sterile demineralized water | qsp 100% |

| Moisturizing anti-ageing lotion for dry skin | |
|---|---|
| Ceramide-type compound of formula (I) | 0.25% |
| Ethanol | 10.00% |
| Perfume | 0.50% |
| Preservative | 0.40 |
| Sterile demineralized water | qsp 100% |

| Alcoholic lotion for nail care | |
| --- | --- |
| Ceramide-type compound of formula (I) | 0.20% |
| Dimethylsulfoxide | 10.00% |
| Ethanol | 40.00% |
| Antioxidant | 0.10% |
| Perfume | qs |
| Sterile demineralized water | qsp 100% |

The invention claimed is:

1. A process for the synthesis of a ceramide-type of the formula

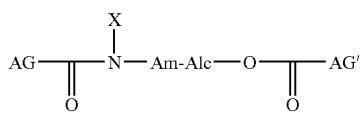 (I)

wherein Am-Alc is alkyl of 2 to 6 carbon atoms derived from an amino alcohol, X is hydrogen or alkyl of 1 to 4 carbon atoms optionally hydroxylated in the 2' position and AG and AG' are individually unsaturated or saturated hydrocarbon of 4 to 30 carbon atoms derived from a fatty acid or fatty acid amide comprising reacting on amino alcohol of the formula AmAlcOH with an acid of the formula AG-COOH wherein AG is defined as above in the presence of a lipase B-type enzyme of *Candida antarctica* to introduce the

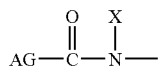

group and with an AG'-COOH wherein AG' is defined as above in the presence of *Rhizomucor miehei* lipase to introduce the

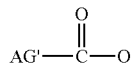

group.

2. The process of claim 1, wherein the amide formation step is carried out under stoechiometric conditions between the fatty acid or the amino-alcohol at a temperature comprised of 40 to 100° C.

3. The process of claim 1, wherein the amide formation is carried out without solvent at a temperature of about 65° C.

4. The process of claim 1, wherein the amide formation is carried out under a reduced pressure of 1 to 500 mbars during at least 16 hours.

5. The process of claim 1, wherein the esterification reaction is carried out with a ratio fatty acid to amino-alcohol of 1 to 2.

6. The process of claim 1, wherein the esterification reaction is carried out at a temperature of 40 to 90° C.

7. The process of claim 1, wherein the esterification reaction is carried out without solvent at a temperature of about 65° C.

8. The process of claim 1, wherein the esterification reaction is carried out under a reduced pressure of 1 to 500 mbars during at least 18 hours.

9. The process of claim 1, wherein the enzymes used in each step are immobilized on an inert support.

10. The process of claim 1, wherein the amide formation reaction with the *Candida antartica* lipase B and the esterification reaction with *Rhizomucor miehei* lipase are both carried out without solvent, optionally simultaneously, at a temperature of about 65° C. and under a reduced pressure of 30 to 200 mbars.

11. The process of claim 1, wherein the starting amino-alcohol corresponds to formula:

 (IV)

in which:

n is 1, 2 or 3 and m is 1, 2 or 3,

X is hydrogen or C1 to C4 carbon chain, optionally hydroxylated on the positions 2' and/or followings of the amino group;

$R^1$ is hydrogen or alkyl of 1 to 4 carbon atoms optionally hydroxylated, $R^2$ is selected from the group consisting of hydrogen, —OH, —NH$_2$ and alkyl of 1 to 4 carbon atoms, optionally hydroxylated, $R^3$ is selected from the group consisting of hydrogen, —OH and —CH$_2$OH, in which at least one of $R^1$, $R^2$ or $R^3$ includes a —OH.

12. The process of claim 1 wherein the amide formation step is performed before the esterification step.

* * * * *